US007705021B2

(12) United States Patent
Khazak et al.

(10) Patent No.: US 7,705,021 B2
(45) Date of Patent: Apr. 27, 2010

(54) ISOINDOLONE COMPOUNDS, COMPOSITIONS CONTAINING THE SAME, AND METHODS OF USE THEREOF FOR THE TREATMENT OF VIRAL INFECTIONS RELATED TO THE ETIOLOGY OF CANCER

(75) Inventors: Vladimir Khazak, Brooklyn, NY (US); Erica A. Golemis, Oreland, PA (US); Sanjay R. Menon, Danbury, CT (US); Lutz Weber, Germering (DE)

(73) Assignee: Fox Chase Cancer Center, Philadelphia, PA (US)

( * ) Notice: Subject to any disclaimer, the term of this patent is extended or adjusted under 35 U.S.C. 154(b) by 293 days.

(21) Appl. No.: 11/412,367

(22) Filed: Apr. 27, 2006

(65) Prior Publication Data

US 2006/0264473 A1 Nov. 23, 2006

Related U.S. Application Data

(60) Provisional application No. 60/676,864, filed on May 2, 2005.

(51) Int. Cl.
*A61K 31/4035* (2006.01)
*A61K 31/44* (2006.01)
*C07D 209/48* (2006.01)
*C07D 213/24* (2006.01)

(52) U.S. Cl. .................. 514/339; 514/414; 546/339; 548/472

(58) Field of Classification Search .................. 548/472
See application file for complete search history.

(56) References Cited

U.S. PATENT DOCUMENTS

2004/0044063 A1* 3/2004 Stockwell et al. ............ 514/418

FOREIGN PATENT DOCUMENTS

WO WO 03/037865 5/2003

OTHER PUBLICATIONS

Advanced Drug Delivery Reviews 48 (2001) 3-26.*
Tetrahedron Letters 39 (1998) 2285-2288.*
CAPLUS, RN 514161-47-3, retrieved on Apr. 23, 2008.*
CAPLUS, RN 19732-69-5, retrieved on Apr. 23, 2008.*
CAPLUS, RN 95646-15-4, retrieved on Apr. 23, 2008.*
CAPLUS, RN 27376-65-4, retrieved on Apr. 23, 2008.*
CAPLUS, RN 68028-26-2, retrieved on Apr. 23, 2008.*
CAPLUS, RN 65422-52-8, retrieved on Apr. 23, 2008.*
CAPLUS, RN 51461-52-0, retrieved on Apr. 23, 2008.*
CAPLUS, RN 861615-18-1, retrieved on Apr. 23, 2008.*
Isomers [online], [retrieved on Mar. 11, 2007]. Retrieved from the internet, URL; http://chemed.chem.purdue.edu/genchem/topicreview/bp/1organic/isomers.html>.*
Viral infections [online], [retrieved on Aug. 9, 2006]. Retrieved from the Internet, URL; http://en.wikipedia.org/wiki/Viral_Infections.*
Medicinal Research Reviews (2004), vol. 24, No. 4, 449-474.*
Journal of Clinical Virology, 2004, vol. 30, 115-133.*
Kikugawa, et al. J. Org. Chem., 2003, 68, 6739-6744.*
Lerner, E.C. et al., "Ras CAAX peptidomimetic FTI-277 selectively blocks oncogenic Ras signaling by inducing cytoplasmic . . . ", J. Biol. Chem., 270: 26802-26806 (1995).
Lyons, J.F. et al., "Discovery of a novel Raf kinase inhibitor", Endocrine-Related Cancer, 8: 219-225 (2001).
Allen, L.F. et al., CI-1040 (PD184352), a targeted signal transduction inhibitor of MEK (MAPKK), Semin. Oncol., 30: 105-116 (2003).
Bhalla, U.S., et al., "MAP Kinase Phosphatase as a Locus of Flexibility in a Mitogen-Activated Protein Kinase Signaling Network", Science, 297: 1018-1023 (2002).
Hoffman, J., "Modulation of Protein Kinase C in Antitumor Treatment", Rev. Physiol. Biochem. Pharmacol., 142: 1-96 (2001).
Wang, X. et al., "Regulation of phorbol ester-mediated TRAF1 induction in human colon cancer cells through a PKC/RAF/ERK/NF . . . ", Oncogene, 23: 1885-1895 (2004).
Herbst, R. et al., "Gefitinib—a novel targeted approach to treating cancer", Nat. Rev. Cancer, 4: 956-965 (2004).
Attoub, S. et al., "The c-kit Tyrosine Kinase Inhibitor STI571 for Colorectal Cancer Therapy", Cancer Res., 62: 4879-4883 (2002).
Murphy, G.A. et al., "Involvement of Phosphatidylinositol 3-Kinase, but not RalGDS, in TC21/R-Ras2-mediated Transformation", J. Biol. Chem., 277: 9966-9975 (2002).
Safran, H. et al., "Herceptin and Gemcitabine for Metastatic Pancreatic Cancers . . . ", Cancer Investigation, 22: 706-712 (2004).
Boni, J.P. et al., "Population pharmacokinetics of CCI-779: Correlations to safety and pharmacogenomic . . . ", Clin. Pharmacol. Ther., 77: 76-89 (2005).
Pruitt, K. et al., "Raf-independent Deregulation of p38 and JNK Mitogen-activated Protein Kinases Are Critical . . . ", J. Biol. Chem., 277: 31808-31817 (2002).
Sehouli, J., "Review of gemcitabine-based combinations for platinum-resdistant ovarian cancer", Int. J. Gynecol. Cancer, 15: 23-30 (2005).
Safran, H. et al., "Trastuzumab, Paclitaxel, Cisplatin, and Radiation for Adenocarcinoma of the Esophagus . . . ", Cancer Investigation, 22: 670-677 (2004).
Montaner, S. et al., "The Kaposi's sarcoma-associated herpesvirus G protein-coupled receptor promotes endothelial cell survival . . . ", Cancer Res., 61: 2641-2648 (2001).
Montaner, S. et al., "The small GTPase Rac1 links the Kaposi sarcoma-associated herpesvirus vGPCR to cytokine . . . ", Blood, 104: 2903-2911 (2004).
Dadke, D. et al., "Activation of p21-Activated Kinase 1-Nuclear Factor kB signaling by Kaposi's Sarcoma-Associated Herpes Virus G . . . ", Cancer Res., 63: 8837-8847 (2003).
Kato-Stankiewicz, J. et al., "Inhibitors of Ras/Raf-1 interaction identified by two-hybrid screening revert . . . ", PNAS, 99: 14398-14403 (2002).
Lo, A.K. et al., "Alterations of Biologic Properties and Gene Expression in Nasopharyngeal Epithelial Cells by the Epstein-Barr . . . ", Lab. Invest., 83: 697-709 (2003).
Roberts, M.L. et al., "Activation of a Ras-MAPK-Dependent Pathway by Epstein-Barr Virus Latent Membrane Protein 1 . . . ", Virology, 240: 93-99 (1998).

(Continued)

*Primary Examiner*—Rebecca L Anderson
*Assistant Examiner*—Shawquia Young
(74) *Attorney, Agent, or Firm*—Dann, Dorfman, Herrell and Skill, P.C.; Patrick J. Hagan

(57) ABSTRACT

Isoindolone derivatives, compositions containing the same, and methods of use thereof for the treatment or prophylaxis of viral infection are disclosed.

11 Claims, 3 Drawing Sheets

OTHER PUBLICATIONS

Kaye, K.M. et al., "Tumor necrosis factor receptor associated factor 2 is a mediator of NF-kB activation . . . ", Proc. Natl. Acad. Sci. USA, 93: 11085-11090 (1996).

Stockl, L. et al., "INtegrity of c-Raf-1/MEK signal transduction cascade is essential for hepatitis B virus gene expression", Oncogene, 22: 2604-2610 (2003).

Benn, J. et al., "Hepatitis B virus HBx protein activates Ras-GTP complex formation and establishes a Ras, Raf, MAP . . . ", Proc. Natl. Acad. Sci. USA, 91: 10350-10354 (1994).

Chung, T.W. et al., "Hepatitis B viral HBx induces matrix metalloproteinase-9 gene expression through . . . ", FASEB J., 18: 1123-1225 (2004).

Klein, N.P. et al., "Activation of Src Family Kinases by Hepatitis B Virus HBx Protein and Coupled Signaling to Ras", Mol. Cell. Biol., 17: 6427-6436 (1997).

Noh, E.J. et al., "Subcellular localization and transcriptional repressor activity of HBx No. p21 . . . ", Biochem. Biophys. Res. Commun., 319: 738-745 (2004).

* cited by examiner

ISOINDOLONE COMPOUNDS, COMPOSITIONS CONTAINING THE SAME, AND METHODS OF USE THEREOF FOR THE TREATMENT OF VIRAL INFECTIONS RELATED TO THE ETIOLOGY OF CANCER This application claims priority to U.S. Provisional Application 60/676,864 filed May 2, 2005, which is incorporated herein by reference.

FIELD OF THE INVENTION

The present invention relates to the fields of virology and cellular signaling. More specifically, the invention provides compounds, compositions and methods useful for the treatment of viral infections, particularly those caused by herpes viruses.

BACKGROUND OF THE INVENTION

A number of publications and patent documents are cited throughout the specification in order to describe the state of the art to which this invention pertains. Each of these citations is incorporated by reference in this application as though set forth herein in full.

Human herpes virus-8 (HHV-8) is a recently identified virus that has been associated with Kaposi's sarcoma (KS) and possibly with a type of cancer called body cavity lymphoma (a tumor that arises from the lymph tissue) (1). HHV-8, also known as Kaposi's sarcoma-associated herpes virus (KSHV), is an important pathogen capable of causing disease that affects all age groups worldwide (2). KS is an unusual skin tumor that is seen primarily in HIV-infected men. HHV-8 has also been isolated in the semen of HIV infected individuals. Because of these factors, it is believed that HHV-8 may cause a sexually transmitted infection.

From the beginning of the AIDS epidemic, it was suspected that there might be another infectious agent besides HIV that causes KS. In the 1980's, around 30-40% of homosexual men with AIDS developed KS at some point in their illness. In contrast, KS was a rare occurrence in women or hemophiliacs with HIV. This suggested that there was an additional factor among gay and bisexual men that increased their risk of developing KS. In 1994, HHV-8, which was previously unknown, was identified by researchers in KS biopsies (3). This virus belongs to the important family of human herpesviruses that includes varicella-zoster (chickenpox/shingles), epstein-barr virus (mononucleosis), and herpes simplex 1 and 2 (oral and genital herpes). After identification of HHV-8, researchers have been able to identify this virus in virtually all types of KS tumors, including those seen before the AIDS epidemic.

The complete HHV-8 genome sequence has sequence similarities to the sequences of other gammaherpesviruses, including herpesvirus saimiri (HVS), murine gammaherpesvirus 68 (MHV68) and Epstein-Barr Virus (HHV-4). The ~165 kb genome contains over 80 open reading frames arranged in a long unique region flanked by multiple 801 bp terminal repeat units of high G+C content. The long unique region contains blocks of conserved genes found in most herpesviruses, interspersed with blocks of non-homologous genes that are specific for HHV-8 and related viruses.

The pathogenic mechanism by which HHV-8 induces tumorigenicity is presently unknown. However, HHV-8 encodes a G-protein coupled receptor (GPCR) that acts as an oncogene, the expression of which causes malignant transformation of rodent fibroblast cells, and produces tumors in nude mice. Transgenic mice expressing the HHV-8-GPCR develop highly vascular endothelial tumors (4-6). Such tumorigenicity relates to the ability of the HHV-8-GPCR to constitutively activate the extracellular signal-regulated kinase (ERK) signal-transduction cascade (7),(8). One of the main activators of the ERK cascade is the Ras-Raf-MEK1/2-ERK signaling axis (9). Further, in some cases, GPCRs are known to signal through Ras (10-12). Inasmuch as a number of viruses utilize this signaling axis to establish infection, agents, which disrupt this pathway should prove efficacious against viruses, which include, for example, Epstein Bar Virus and Hepatitis B virus.

Clearly a need exists for compositions and methods useful for treating viral infections, including KSHV. The present application provides such compositions and methods.

SUMMARY OF THE INVENTION

In accordance with one aspect, the present invention provides compounds, including isomers having the formula:

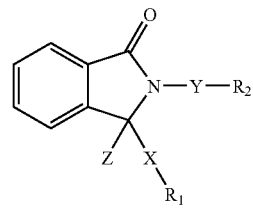

(I)

wherein

X is $(CH_2)_n$, CO, $SO_2$, CONH or a valence bond;

Y is $(CH_2)_n$, CO, $SO_2$ or CONH;

Z is H, —OH, alkoxy n is 0, 1, 2, 3, 4 or 5;

R1 is an optionally substituted aryl, aralkyl, heteroaryl or heteroarylalkyl;

R2 is an optionally substituted heteroalkyl, aryl, aralkyl, heteroaryl, heteroaralkyl, cycloalkyl, heterocycloalkyl or heteroalkylcycloalkyl group, the pharmacologically acceptable salts of such compounds and the solvates thereof.

According to another aspect, the present invention provides pharmaceutical compositions comprising one or more of the above-described isoindolone derivatives in combination with a pharmaceutically acceptable carrier medium. In one embodiment, the composition further comprises at least one agent or inhibitor selected from the group provided in Table II in a pharmaceutically acceptable carrier.

In accordance with yet another aspect, the present invention provides a method for treating viral infections in mammalian hosts by administering to a subject in need of such treatment an effective amount of the above-described compound or composition.

In accordance with still another aspect, the invention provides a method for prophylaxis and/or treatment of viral infection in a host susceptible to said infection. In one embodiment the method comprises administration of a therapeutically effective amount of the above mentioned compound, and optionally at least one mitogen activated protein kinase (MAPK) pathway inhibitor and/or an antiproliferative agent.

DETAILED DESCRIPTION OF THE INVENTION

Figure 1:
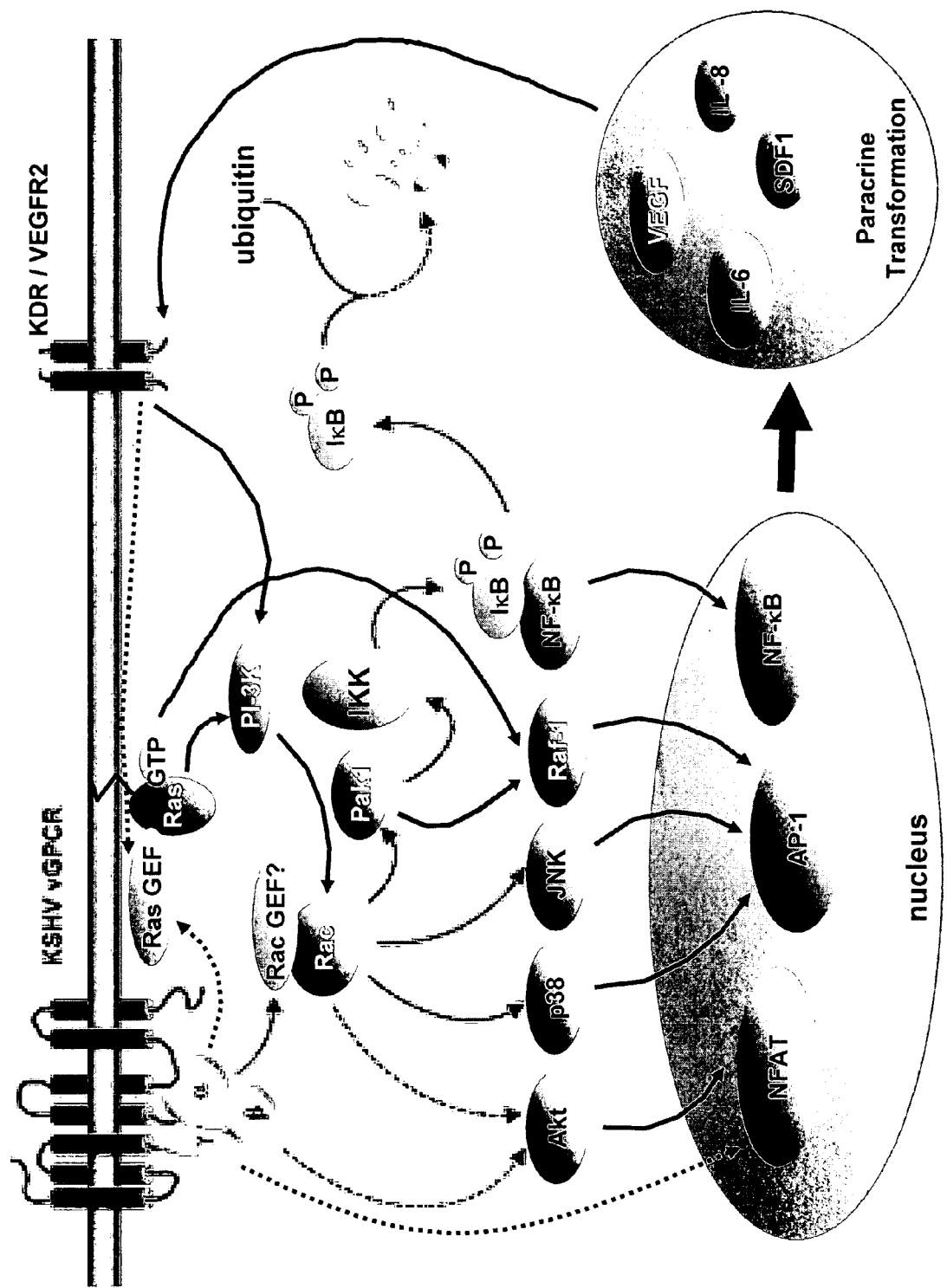
FIG. 1 is a schematic of the signaling cascade that leads to cellular transformation associated with KSHV infection.

Recently, a new class of protein-protein interaction inhibitors, represented by formula (I) above has been synthesized. These include
3-(4-Benzyloxy-3-methoxy-phenyl)-3-methoxy-2-(2-pyridin-2-yl-ethyl)-2,3-dihydro-isoindol-1-one (7);
3-(4-Benzyloxy-3-methoxy-phenyl)-2-(2-pyridin-2-yl-ethyl)-2,3-dihydro-isoindol-1-one (8); and
2-(4-benzyloxy-3-methoxy-benzyl)-3-(2-pyridin-2-yl-methyl)-2,3-dihydro-isoindol-1-one (11).

The compounds of the invention block interaction between the human Ras and Raf oncoproteins, and inhibit various oncogenic phenotypes associated with activated Ras (13, PCT/EP02/1222 (WO 03/037865)). The (MAPK) pathway comprising the Ras/Raf/Mek/Erk cellular signaling module plays a key role in the transduction of extracellular growth factor stimuli to the nucleus, ultimately resulting in changes in gene expression. As a result, the regulation of the MAPK pathway is considered to be highly pertinent to the control of a variety of biological processes, including cell proliferation, differentiation, survival and apoptosis.

The compounds described herein block the interaction between Ras and Raf and thus should have demonstrable efficacy as antiviral agents. Based on previously identified signaling cascades, such viruses include without limitation, HHV-8, HHV-4 and hepatitis B virus. Furthermore, the compounds used in the practice of this invention can be combined with other known anti-viral or anti-proliferative agents in methods of treating or preventing viral infection.

Compounds useful in the practice of the present invention include those of Formula (I):

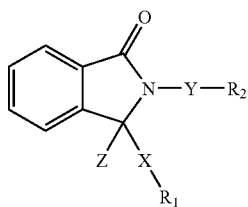

X is $CH_2$, CO, $SO_2$ CONH or a valence bond;
Y is $(CH_2)_n$, CO, $SO_2$ or CONH;
Z is H, —OH, alkoxy,
n is 0, 1, 2, 3, 4 or 5;
R1 is an optionally substituted aryl, aralkyl, heteroaryl or heteroaralkyl;
R2 is an optionally substituted heteroalkyl, aryl, aralkyl, heteroaryl, heteroaralkyl, cycloalkyl, heterocycloalkyl or heteroalkylcycloalkyl The term alkyl, as used herein, refers to a saturated or unsaturated (i.e. alkenyl and alkynyl) straight or branched chain alkyl group, containing from one or two to ten carbon atoms, preferably from one or two to six carbon atoms, e.g. 1 or 2 to 4 carbon atoms, for example methyl, ethyl, propyl, iso-propyl, butyl, iso-butyl, tert.-butyl, n-hexyl, 2,2-dimethylbutyl, n-octyl, ethenyl(vinyl), propenyl, iso-propenyl, butenyl, isoprenyl or hexa-2-enyl; ethynyl, propynyl or butynyl groups.

The terms alkenyl and alkynyl, as used herein, refer to unsaturated straight or branched chain alkyl groups, containing from two to ten carbon atoms, preferably from two to six carbon atoms, e. g. 2 to 4 carbon atoms, for example ethenyl (vinyl), propenyl, iso-propenyl, butenyl, isoprenyl or hexa-2-enyl; ethynyl, propynyl or butynyl groups.

The term heteroalkyl, as used herein, refers to an alkyl, alkenyl or alkynyl group as defined above where one or more carbon atoms are replaced by an oxygen, nitrogen, phosphorous or sulphur atom, for example an alkoxy group containing from one to ten carbon atoms, preferably from one to six carbon atoms, e.g. 1 to 4 carbon atoms, such as methoxy, ethoxy, propoxy, iso-propoxy, butoxy or tert.-butoxy, a (1-4C)alkoxy(1-4C)alkyl group such as methoxymethyl, ethoxymethyl, 1-methoxyethyl, 1-ethoxyethyl, 2-methoxyethyl or 2-ethoxyethyl; or a cyano group. The term heteroalkyl furthermore refers to a group derived from a carboxylic acid or carboxylic acid amide containing from one to ten carbon atoms, preferably from one to six carbon atoms, e.g. 1 to 4 carbon atoms, and may, for example, be acyl containing from one to ten carbon atoms, preferably from one to six carbon atoms, e.g. 1 to 4 carbon atoms, such as acetyl, propionyl, butyryl or pivaloyl; acyloxy containing from one to ten carbon atoms, preferably from one to six carbon atoms, e.g. 1 to 4 carbon atoms such as acetyloxy, propionyloxy, butyryloxy or pivaloyloxy; carboxyalkyl containing from one to ten carbon atoms, preferably from one to six carbon atoms, e.g. 1 to 4 carbon atoms such as carboxymethyl, carboxyethyl, carboxypropyl, carboxybutyl, carboxyalkyl ester containing from one to ten carbon atoms, preferably from one to six carbon atoms, e.g. 1 to 4 carbon atoms, such as carboxyalkyl methyl ester, carboxyalkyl ethyl ester, carboxyalkyl propyl ester, carboxyalkyl isopropyl ester, carboxyalkyl butyl ester or carboxyalkyl tert.-butyl ester, carboxyalkyl amide or alkylcarbamoyl such as N-(1-4C)alkylcarbamoyl or N,N'-(1-4C)dialkylcarbamoyl) containing from one to ten carbon atoms, preferably from one to six carbon atoms, e.g. 1 to 4 carbon atoms such as N-methylcarbamoyl, N-ethylcarbamoyl, N-propylcarbamoyl, N,N'-dimethylcarbamoyl, N-ethyl-N-methylcarbamoyl or N,N'-dipropylcarbamoyl, alkoxycarbonyl containing from one to ten carbon atoms, preferably from one to six carbon atoms, e.g. 1 to 4 carbon atoms, such as methoxycarbonyl, ethoxycarbonyl, propoxycarbonyl, isopropoxycarbonyl, butoxy- or tert.-butoxycarbonyl or alkoxycarbonyloxy containing from one to ten carbon atoms, preferably from one to six carbon atoms, e. g. 1 to 4 carbon atoms such as methoxycarbonyloxy, ethoxycarbonyloxy, propoxycarbonyloxy, isopropoxycarbonyloxy, butoxycarbonyloxy, tert.-butoxycarbonyloxy.

The term cycloalkyl, as used herein, refers to a saturated or partially unsaturated cyclic group, having one or more rings, formed by a skeleton that contains from three to 14 carbon atoms, preferably from three, four, five or six to nine or ten carbon atoms, for example cyclopropyl, cyclobutyl, cyclopentyl, cyclohexyl, tetralin, cyclopentenyl or cyclohex-2-enyl groups.

The term heterocycloalkyl, as used herein, refers to a cycloalkyl group as defined above where one or more carbon atoms are replaced by one or more oxygen, nitrogen, phosphorous or sulphur atoms. Specific examples for heterocyclalkyl are piperidino, morpholino, N-methyl-piperazino or N-phenyl-piperazino groups.

The term aryl, as used herein, refers to an aromatic cyclic group, having one or more rings, formed by a skeleton that contains from five to 14 carbon atoms, preferably from five or six to nine or ten carbon atoms, for example phenyl, indenyl or naphthyl groups. Specific examples are a benzyl, tolyl, phenethyl, biphenyl, xylyl, cumyl, 2-, 3-or 4-methoxyphenyl, 2-, 3-or 4-ethoxyphenyl, 4-carboxyphenyl or a 4-hydroxyphenyl group.

The term heteroaryl, as used herein, refers to an aryl group as defined above where one or more carbon atoms are replaced by an oxygen, nitrogen, phosphorous or sulphur atom, for example 4-pyridyl, 2-imidazolyl, 3-pyrazolyl, quinolinyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyridinyl, pyrimidinyl and pyridazinyl groups.

The terms aralkyl and heteroaralkyl, as used herein, refer to groups that comprise both aryl or, respectively, heteroaryl as well as alkyl, alkenyl, alkynyl and/or heteroalkyl (for example alkoxy groups in case of aralkyloxy) and/or cycloalkyl and/or heterocycloalkyl ring systems as defined herein. Examples of such groups are arylalkyl-, arylalkenyl-, arylalkinyl-, arylheteroalkyl-, arylheteroalkenyl-, arylheteroalkinyl-, heteroarylheteroalkyl-, heteroarylheteroalkenyl-, heteroarylheteroalkinyl-, arylcycloalkyl-, heteroaryl-cycloalkyl-, arylheterocycloalkyl-, heteroarylheterocycloalkyl-, arylcycloalkenyl-, heteroarylcycloalkenyl-, arylcycloalkinyl-, heteroarylcycloalkinyl-, arylheteroalkenyl-, heteroarylheteroalkenyl-, arylheteroalkinyl-, heteroarylheteroalkinyl-, heteroarylalkyl-, heteroalkenyl- and heteroarylakinyl-groups, wherein the cyclic groups can be saturated or once, twice or three-times unsaturated. Examples are the tetrahydroisoquinolinyl, benzyl, benzyloxy, 2-or 3-ethyl-indolyl or 4-methylpyridino groups.

The term heteroalkylcycloalkyl, as used herein, refers to groups that comprise heterocycloalkyl as well as alkyl, alkenyl, alkynyl and/or heteroalkyl (for example alkoxy groups in case of aralkyloxy) groups, as defined above. Examples of such groups are alkylheterocycloalkyl, alkenylheterocycloalkyl, alkinylheterocycloalkyl, heteroalkylcycloalkyl, heteroalkenylcycloalkyl, heteroalkinylcycloalkyl, heteroalkylheterocycloalkyl, heteroalkenylheterocylcloalkyl, heteroalkinylheterocycloalkyl, which cyclic groups can be saturated or once, twice or three-times unsaturated.

Any alkyl, alkenyl, alkynyl, heteroalkyl, cycloalkyl, heterocycloalkyl, aryl, heteroaryl aralkyl or heteroarylalkyl groups as defined herein may be substituted with one or more halogen atoms, $NH_2$, SH, $NO_2$ or OH groups or unsubstituted alkyl, heteroalkyl, aryl, aralkyl, aralkyloxy, heteroaryl, cycloalkyl or heterocycloalkyl groups as defined herein.

The term "optionally substituted" refers to the replacement of one or more hydrogen atoms in a chemical moiety by a halogen atom, a $NH_2$, SH, $NO_2$ or OH group or by a unsubstituted alkyl, heteroalkyl, aryl, aralkyl, aralkyloxy, heteroaryl, cycloalkyl or heterocycloalkyl group, as defined herein.

Preferred are compounds of Formula (I), wherein Y is $(CH_2)_n$ and n is 0, 1 or 2.

Further preferred are compounds of Formula (I), wherein R1 is an optionally substituted phenyl ring, particularly preferred being the phenyl ring substituted by a benzyloxy group.

Also preferred are compounds of Formula (I), wherein R2 is heterocycloalkyl or heteroaryl especially preferred being nitrogen-containing heterocycloalkyl or heteroaryl groups.

Further preferred are compounds of Formula (I), wherein R2 is a pyridyl or a piperidyl group.

Also preferred are compounds of formula (I), wherein R1 is a group of the formula

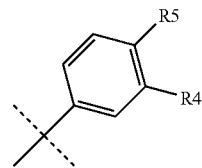

wherein R4 is H, alkyloxy or aralkyloxy (more preferably H, methoxy or benzyloxy) and R5 is F, Cl, alkyl, heteroalkyl, aryl, aralkyl, heteroaryl or heteroarylalkyl (preferred Cl, methoxy or benzyloxy; more preferably benzyloxy).

Further preferred are compounds, including isomers, having the Formula:

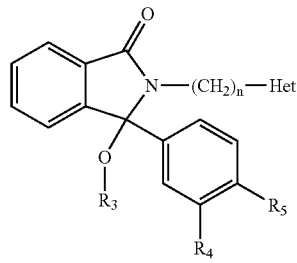

wherein Het is a pyridyl group; n is 0, 1 or 2; $R_3$ is alkyl; $R_4$ is H, alkoxy or aralkoxy (more preferably H, methoxy or benzyloxy) and $R_5$ is F, Cl, alkyl, heteroalkyl, aryl, aralkyl, heteroaryl or heteroarylalkyl (preferably Cl, methoxy or benzyloxy; more preferably benzyloxy) group, and the pharmacologically acceptable salts of such compounds and the solvates thereof.

Also preferred are compounds of Formula (II), wherein Het is a piperidyl group; n is 0, 1 or 2; $R_3$ is alkyl; $R_4$ is H, alkyl or aralkoxy (more preferably H, methoxy or benzyloxy) and $R_5$ is F, Cl, alkyl, heteroalkyl, aryl, aralkyl, heteroaryl or heteroarylalkyl (preferably Cl, methoxy or benzyloxy; more preferably benzyloxy).

Especially preferred are the following compounds:
3-(4-Benzyloxy-3-methoxy-phenyl)-3-methoxy-2-(2-pyridin-2-yl-ethyl)-2,3-dihydro-isoindol-1-one (7);
3-(4-Benzyloxy-3-methoxy-phenyl)-2-(2-pyridin-2-yl-ethyl)-2,3-dihydro-isoindol-1-one (8); and
2-(4-benzyloxy-3-methoxy-benzyl)-3-(2-pyridin-2-yl-methyl)-2,3-dihydro-isoindol-1-one (11).

It should be appreciated that compounds of Formula (I) or (II) may have different geometrical isomers (which are usually denoted as cis/trans isomers or more generally as (E) and (Z) isomers) or different optical isomers as a result of one or more asymmetric or chiral carbon atoms (which are usually nomenclatured under the Cahn-Ingold-Prelog or R/S system) and may be produced as mixtures of diastereomers, mixtures of enantiomers or as optically pure compounds. The compounds described herein may also exist in tautomeric forms from which only one might be specifically mentioned or depicted in the present specification. Further, some compounds may display polymorphism. All these geometrical or optical isomers (as well as racemates and diastereomers), tautomeric forms and polymorphous forms are included in the invention.

The present invention also relates to pharmacologically acceptable salts, or solvates and hydrates, respectively, and to compositions and formulations of compounds of Formula (I) or (II). The pharmaceutical compositions according to the present invention contain at least one compound of Formula (I) or (II) as the active agent and optionally carriers and/or diluents and/or adjuvants. Examples of such pharmacologically acceptable salts of sufficiently basic compounds of Formula (I) or (II) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleinic and salicylic acid. Further, a sufficiently acid compound of Formula (I) or (II) may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, N-methyl-D-aminomethane (meglumin), piperidine, morpholine, tris-(2-hydroxyethyl) amine, lysine or arginine salts. Compounds of Formula (I) or (II) may be solvated, especially hydrated. The hydratisation can occur during the process of production or as a consequence of the hygroscopic nature of the initially water free compounds of Formula (I) or (II).

The present invention also relates to pro-drugs which are composed of a compound of Formula (I) or (II) and at least one pharmacologically acceptable protective group which will be cleaved off under physiological conditions, such as an alkoxy-, aralkyloxy-, acyl- or acyloxy group as defined herein, e.g. ethoxy, benzyloxy, acetyl or acetyloxy.

As mentioned above, therapeutically useful agents that contain compounds of Formula (I) or (II), their solvates, salts and formulations are also included in the scope of the present invention. In general, compounds of Formula (I) or (II) will be administered by using the acceptable modes known in the art, either alone or in combination with any other therapeutic agent. Such therapeutically useful agents can be administered by one of the following routes: oral, e. g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e. g. as an injectable solution or suspension, rectal as suppositories, by inhalation or insufflation, e. g. as a powder formulation, as microcrystals or as a spray (e. g. liquid aerosol), transdermal, for example via an transdermal delivery system (TDS) such as a plaster contaning the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e. g. lactose, sucrose, glucose, gelatin, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use excipients as are e.g. water, alcohols, aqueous saline, aqueous dextrose, polyols, glycerin, vegetable, petroleum, animal or synthetic oils. For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilisation, e.g. UV stabilizers, emulsifiers, sweetener, aromatisers, salts to change the osmotic pressure, buffers, coating additives and antioxidants.

Combinations with other therapeutic agents may include other therapeutically useful agents, such as those used to prevent or treat cancer. A list of exemplary agents is provided herein lower.

The following examples are provided to illustrate various embodiments of the invention. They are not intended to limit the invention in any way.

EXAMPLE 1

A representative example of a compound having the structure of formula (I) in which X represents a valence bond, $R_1$ represents 3-methoxy-4-benzyloxyphenyl, Y represents ethylene, $R_2$ represents pyridine and Z represents hydroxyl, hydrogen or methoxy, can be synthesized as shown in Scheme 1, below.

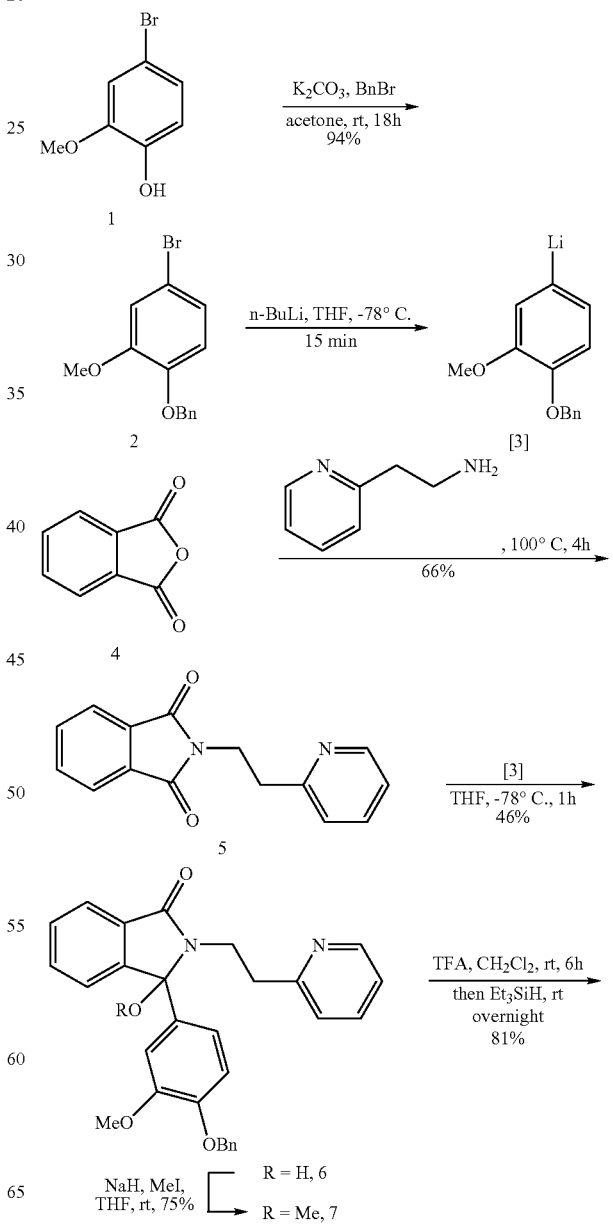

-continued

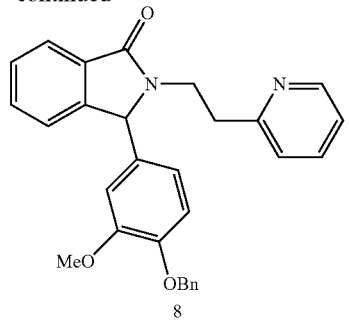
8

Reaction scheme 1 is carried out as follows.

1-Benzyloxy-4-bromo-2-methoxy-benzene (2): A mixture of bromo phenol 1 (10.0 g, 49.2 mmol), $K_2CO_3$ (10.2 g, 73.9 mmol) and benzyl bromide (6.2 mL, 51.7 mmol) in acetone (100 mL) was stirred at room temperature for 18 h. Volatiles were evaporated to yield 2 (14.7 g, 94%) as a colorless syrup which upon standing transformed into a white solid.

2-(2-Pyridin-2-yl-ethyl)-isoindol-1,3-dione (5): A mixture of phthalic anhydride 4 (5.0 g, 33.7 mmol) and pyridylethylamine (4.04 mL, 33.7 mmol) were heated together at 100° C. for 4 h. The resulting red oil upon cooling to room temperature yielded an off-white solid that was filtered and dried under vacuum to provide 5 as a white solid (5.6 g, 66%).

3-(4-Benzyloxy-3-methoxy-phenyl)-3-hydroxy-2-(2-pyridin-2-yl-ethyl)-2,3-dihydro-isoindol-1-one (6): A solution of 2 (4.0 g, 13.7 mmol) in dry THF (40 mL) at −78° C. was treated with n-BuLi (2.5 M, 6.0 mL, 15.0 mmol) for 15 min to produce 3. To this solution, 5 (3.1 g, 12.2 mmol) in dry THF (40 mL) was added slowly over a 10 min period. The reaction mixture turned light brown in color and stirring was continued for 1 h. The reaction was quenched by the addition of saturated aqueous $NH_4Cl$ (10 mL) and the organic layer was separated. The aqueous layer was extracted with EtOAc (3×25 mL) and the combined organic layer was washed with brine (15 mL). Volatiles were evaporated under reduced pressure and the crude residue was purified by column chromatography using 20% acetone/hexane as the eluent to afford the title compound 6 as a white solid (2.6 g, 46%).

3-(4-Benzyloxy-3-methoxy-phenyl)-3-methoxy-2-(2-pyridin-2-yl-ethyl)-2,3-dihydro-isoindol-1-one (7): To a solution of 6 (0.20 g, 0.43 mmol) in dry THF (3 mL) at 0° C., NaH (60%, 0.021 g, 0.86 mmol) was added. After the mixture was stirred for 30 min, MeI (54 μL, 0.86 mmol) was added and stirring was continued overnight at room temperature. The reaction was quenched by the addition of saturated aqueous $NH_4Cl$ (0.5 mL). Solvent was evaporated under reduced pressure and the residue was extracted with $CH_2Cl_2$ (2×10 mL). The combined organic layer was washed with $H_2O$ (3 mL), brine (3 mL) and then dried over anhydrous $Na_2SO_4$. Solvent was evaporated under reduced pressure and the residual red syrup was purified by column chromatography using 35% acetone/hexane as the eluent to provide 7 (0.16 g, 75%) as a light yellow syrup.

3-(4-Benzyloxy-3-methoxy-phenyl)-2-(2-pyridin-2-yl-ethyl)-2,3-dihydro-isoindol-1-one (8): To a solution of 6 (0.50 g, 1.07 mmol), in $CH_2Cl_2$ (5 mL) at room temperature, trifluoroacetic acid (1.0 mL) was added and the reaction mixture was stirred for 6 h. $Et_3SiH$ (0.34 mL, 2.14 mmol) was added to the reaction mixture and the resulting pink solution was stirred overnight at room temperature. Solvent was evaporated under reduced pressure and the residue was neutralized with aqueous $NaHCO_3$ solution and extracted with $CH_2Cl_2$ (2×10 mL). The combined organic layer was washed with $H_2O$ (5 mL), brine (5 mL) and then dried over anhydrous $Na_2SO_4$. Solvent was evaporated under reduced pressure and the residual light yellow syrup was purified by column chromatography using 20% acetone/hexane as the eluent to afford the title compound 8 (0.39 g, 81%) as a white solid.

A representative example of a compound having the structure of formula (I) in which X and Y represent methylene, $R_1$ represents pyridine, $R_2$ represents 3-methoxy-4-benzyloxyphenyl and Z represents hydrogen may be synthesized as shown in Scheme 2, below.

Scheme 2

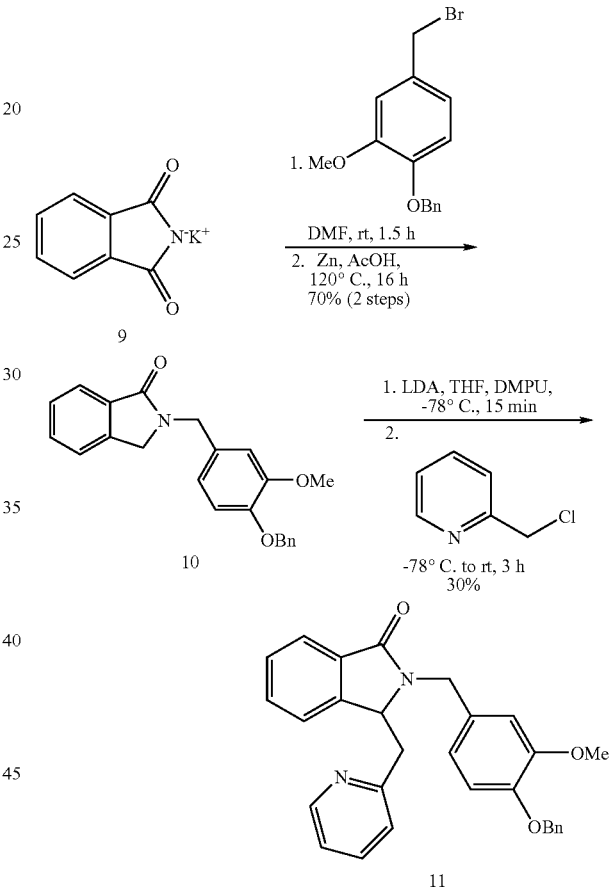

Reaction scheme 2 is carried out as follows:

2-(4-benzyloxy-3-methoxy-benzyl)-2,3-dihydro-isoindol-1-one (10): A solution of (4-benzyloxy-3-methoxy)-benzylbromide (0.92 g, 3.0 mmol) in DMF (12 mL) was treated with potassium phthalimide 9 (0.61 g, 3.6 mmol) and the resulting mixture was stirred at room temperature for 1.5 h when TLC showed absence of starting halide. The reaction mixture was concentrated under reduced pressure. The residue was dissolved in $CH_2Cl_2$ (50 mL), washed with $H_2O$ (2×20 mL), brine (20 mL), dried over anhydrous $Na_2SO_4$ and concentrated under reduced pressure to yield the crude N-alkylated imide (1.33 g) which was directly carried on to the next step without further purification. A solution of the so obtained crude N-alkylated imide (1.2 g, 3.0 mmol) in acetic acid (7.5 mL) was treated with zinc dust (1.96 g, 30 mmol) and the resulting mixture was heated and stirred at 120° C. for 16 h. After solids were removed by filtration, the filtrate was concentrated under reduced pressure. The residue was dissolved in $CH_2Cl_2$ (100 mL), washed with saturated aqueous $NaHCO_3$ (2×25 mL), brine (25 mL), dried over anhydrous $Na_2SO_4$ and concentrated under reduced pressure. The crude product was purified by silica gel chromatography using a solvent mixture of EtOAc/hexanes (2:3) as eluent to afford 10 (0.755 g, 70% over two steps).

2-(4-benzyloxy-3-methoxy-benzyl)-3-(2-pyridin-2-yl-methyl)-2,3-dihydro-isoindol-1-one (11):

A solution of 10 (0.16 g, 0.44 mmol) in 1,3-dimethyl-3,4,5,6-tetrahydro-2(1H)-pyrimidone (DMPU) (1 mL) and THF (2 mL) was cooled to −78° C., treated with lithium diisopropylamide (LDA) (2 M, 0.55 mL, 1.1 mmol) and then stirred at −78° C. for 15 min. A solution of picolyl chloride (0.142 g, 1.1 mmol) in DMPU (0.5 mL) and THF (1 mL) was now added at −78° C. and the reaction mixture was warmed up to room temperature during 3 h. The reaction mixture was re-cooled to 0° C., quenched with 10% aqueous $NH_4Cl$ solution and concentrated under reduced pressure. The residue was partitioned between $H_2O$ (20 mL) and $Et_2O$ (50 mL). The aqueous layer was re-extracted with $Et_2O$ (3×50 mL). The combined organic layer was washed with $H_2O$ (3×50 mL), dried over anhydrous $Na_2SO_4$ and concentrated under reduced pressure. The crude product was purified by silica gel chromatography using acetone/hexanes (1:2) as the eluent to yield pure compound 11 (0.060 g, 30%).

EXAMPLE 2

Isoindolone Derivatives Inhibit MAPK Activity

The present example describes assays for assessing MAPK pathway signaling modulation mediated by the compounds and compositions described herein. Specifically, compounds of the invention have been assessed in an ELK-1 luciferase reporter assay in HeLa cells to obtain an $IC_{50}$ measurement as well as to assess their anti-proliferative capacity.

MAPK Signaling Reporter Assay

Following 72 hours of serum starvation, HLR (HeLa Luciferase Reporter)-Elk-1 cells (30,000 cells per well) were incubated for one hour in the presence or absence of various concentration of inhibitors prior to stimulation of Elk1 release by EGF addition (10 ng/ml). The amount of Elk1 release was measured after five hours using Bright-Glo Luciferase assay (Promega Co., Madison, Wis.).

Proliferation Assay

Five thousand HCT-116 cells were seeded into each well of a 96 well flat bottom plate and incubated over night at 37° C. in 5% $CO_2$. The growth of plated cells was measured by adding 7.5 μM WST-1 reagent (Roche Applied Sciences, Germany) to three control wells and measuring OD650 and OD450 absorbances with a SpectraMax250 plate reader. If the OD650-OD450 values were above 0.5, the remainder of the plate was used for incubation with compounds or solvent control for 48 hours. After this incubation, WST-1 reagent was added to the wells and OD650-OD450 values were calculated as before. Triplicate wells were assayed for each condition and standard deviation was determined; all experiments were performed at least three times independently.

Results

The results of the assays described above are provided in Table 1.

TABLE I

INHIBITORY PROPERTIES OF ISOINDOLONE DERIVATIVES OF THE INVENTION

| Compound | Elk-1 $IC_{50}$ (μM) | Proliferation (HCT-116) $GI_{50}$ (μM) |
|---|---|---|
| A | 20.6 ± 3.8 | 24.7 ± 3.4 |
| B | 0% inhibition at 20 μM | ND |
| 8 | 31.8 ± 6.1 | 21% inhibition at 60 μM |
| 11 | 43.0 ± 6.9 | 26% inhibition at 60 μM |
| 7 | 22.2 ± 6.8 | 22.2 ± 5.3 |

Compounds A and B, are amine derivatives that are included as a basis for comparison of biological activity. Compounds 7, 8 and 11 are the same compounds referred to in Example I above.

As mentioned above, the present invention encompasses methods comprising the combined administration of at least one of the compounds described herein in conjunction with at least one anti-proliferative/cytotoxic agent for inhibiting or preventing viral infection. The following table lists a variety of anti-proliferative and cytotoxic agents that when used in combination with the isoindolones described herein, should have therapeutic efficacy for the treatment of viral infection.

TABLE 2

| Compound | Target | Phenotype/Assay | Reference | Source |
|---|---|---|---|---|
| FTI277 | Farnesyl transferase p-MAPK1,2 level | Proliferation (WST-1) | (13) | Calbiochem |
| Bay43-9006 | Raf-1, B-Raf kinases | Proliferation p-MAPK1,2 level | (14) | Calbiochem |
| CI-1040 | Mek1,2 kinases | Proliferation p-MAPK1,2 level | (15) | Pfizer |
| AA-COCF3 | cPLA2 | Proliferation (WST-1) p-MAPK1,2 level | (16) | Biomol |
| Bryostatin | PKC | Proliferation (WST-1) p-MAPK1,2 level | (17, 18) | Biomol |
| IRESSA | EGFR | Proliferation (WST-1) p-MAPK1,2 level | (19) | FCCC |
| Glivec | BCR/ABL, c-Kit, PDGFR | Proliferation (WST-1) | (20) | Novartis |
| LY294002 | PY3-K | Proliferation (WST-1) p-AKT1,2 level | (21) | Cell Signaling |
| Herceptin | Her-2 | Proliferation (WST-1) | (22) | FCCC |

TABLE 2-continued

| Compound | Target | Phenotype/Assay | Reference | Source |
|---|---|---|---|---|
| Sirolimus (CCI-779) | mTor | Proliferation (WST-1) | (23) | FCCC |
| SP600125 | JNK | Proliferation (WST-1 p-c-JUN level | (24) | Tocris Cookson Bristol, UK |
| Gemcitabine | DNA synthesis | Proliferation (WST-1) | (25) | Ely Lily |
| Paclitaxel | Anti-mitotic, Tubulin polymerization | Proliferation (WST-1) | (26) | Biomol |

Kaposi's sarcoma, caused by HHV-8, is a multifocal angio-proliferative neoplasm induced following long-term infection with Kaposi's sarcoma herpesvirus/human herpesvisrus 8 (KSHV/HHV-8). Development of this neoplasm strictly depends upon the availability of multiple angiogenic growth factors and cytokines, which act in combination from virally encoded oncogenic signals provided by such proteins as the KSHV-encoded viral G-protein coupled receptor (vGPCR). As shown in FIG. 1, vGPCR induction of transformation of KSHV-infected cells involves direct and indirect autocrine/paracrine mechanisms, which requires enhanced expression and secretion of number of angiogenic factors and cytokines. These factors include VEGF, IL-8, IL-6, Gro α(27-29), and potentiate vGPCR signaling by enhancing vGPCR direct transformation effect in autocrine fashion (30,31). Recently, the KSHV-vGPCR was implicated in immortalization of human endothelial HUVEC cells via activation of their VEGF receptor-2/KDR protein (32). Finally, vGPCR induces expression of the cytokines and growth factors by activation of key transcription factors, including AP-1, NF-κB and NF-AT (33,34), through activation of p21-activated kinase-1 (Pak1) that forwards the signaling on Raf-1 and IKK kinases (34). While not wishing to be bound to any particular mechanism of action, the compounds of the invention appear to regulate activation of AP-1 and NF-κB transcription factors induced by oncogenic Ras growth factors and TNF (35), and since Raf and Ras signaling has been shown to be relevant to signal transduction induced by cellular GPCRs (34,35), it is reasonable to believe that interruption of the Ras-Raf interaction will interrupt KSHV-vGPCR-dependent functions. The preliminary data provided herein support this proposed mechanism for KSHV-vGPCR-dependent cell transformation.

Figure 2:
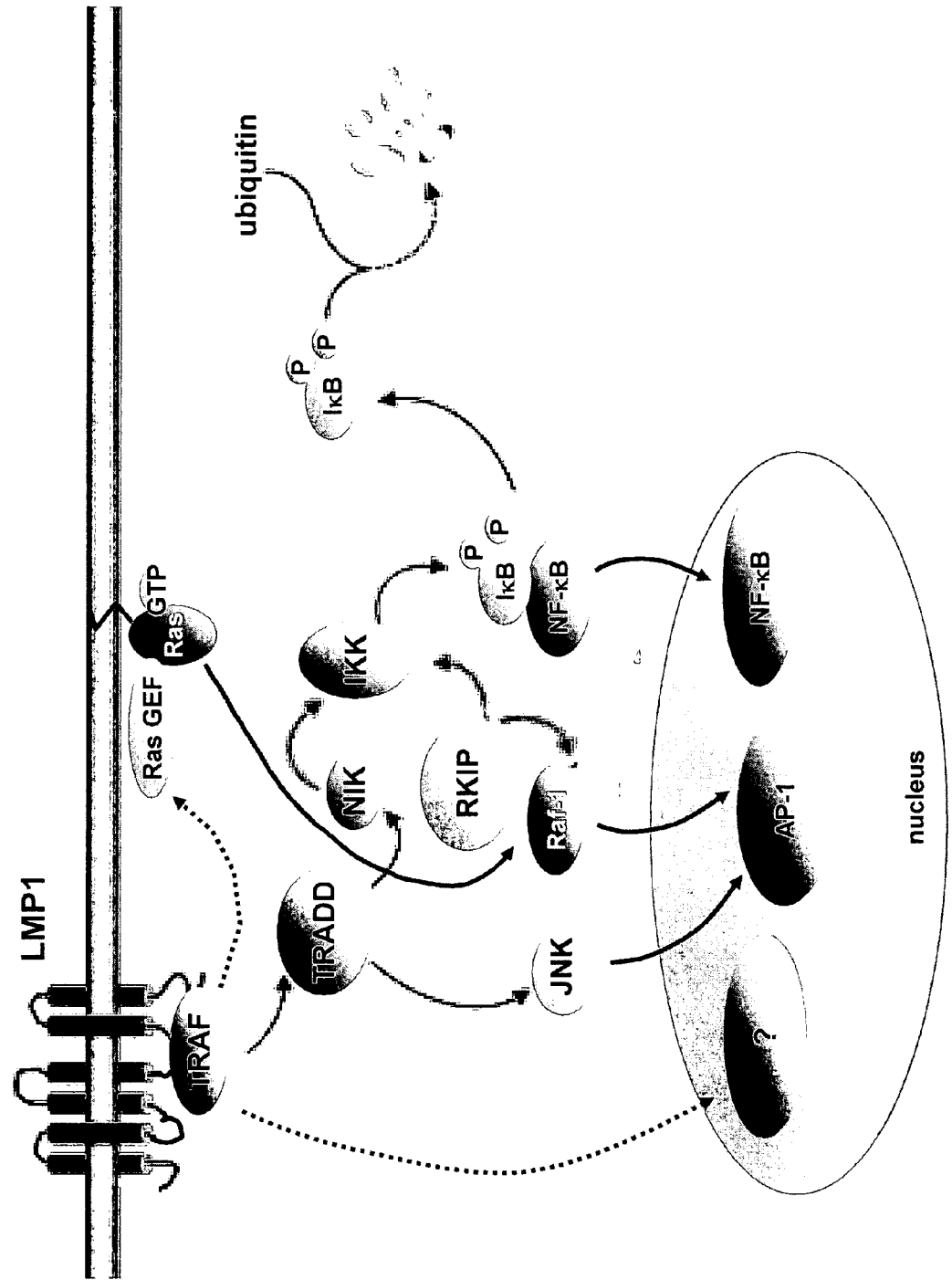
FIG. 2 is a schematic of the signaling cascade that leads to cellular transformation associated with HHV-4/Epstein Barr virus infection.

HHV-4 belongs to the same group of gamma-herpes viruses as KSHV. HHV-4 is associated with a number of malignancies of lymphoid and epithelial origin, including endemic Burkitt's lymphoma, T-cell lymphomas, Hodgkin's disease, undifferentiated nasopharyngeal carcinoma and several other carcinomas (36-39). Like KSHV, the HHV-4 genome is frequently found in the lymphomas and lymphoproliferative disorders of immunocompromised transplant patients and individuals with AIDS (40,41). LMP1, an integral membrane protein expressed by HHV-4 during type 2 and type 3 latent infections, is the only HHV-4 protein that produces a classic oncogenic effect in Rat-1 and NIH3T3 cells, and in B cells (39, 42). An animal model for LMP1 exists, as LMP1 transgenic mice develop lymphomas at increased frequency (43). Significantly, LMP1 produces its effect through activation of two major signaling cascades, the NF-κB pathway and the Ras-MAPK signaling pathway (44-46). See FIG. 2. The induction of these signaling cascades occurs through interaction of cytoplasmic domain of LMP 1 with TRAF and TRADD proteins (46-48) which subsequently signal through the NIK and IKK kinases towards IκB repressor (49). Significantly, the Raf kinase inhibitor protein (RKIP) has been found to also function as a negative regulator of the NFκB pathway (50), and may provide a physical bridge between the two complexes: in any case, this and other data from non-viral systems (51) indicates that the MAPK and NFκB signaling cascades are engaged in significant cross-talk that may be important in specifying the course of HHV-4 infection.

Figure 3:
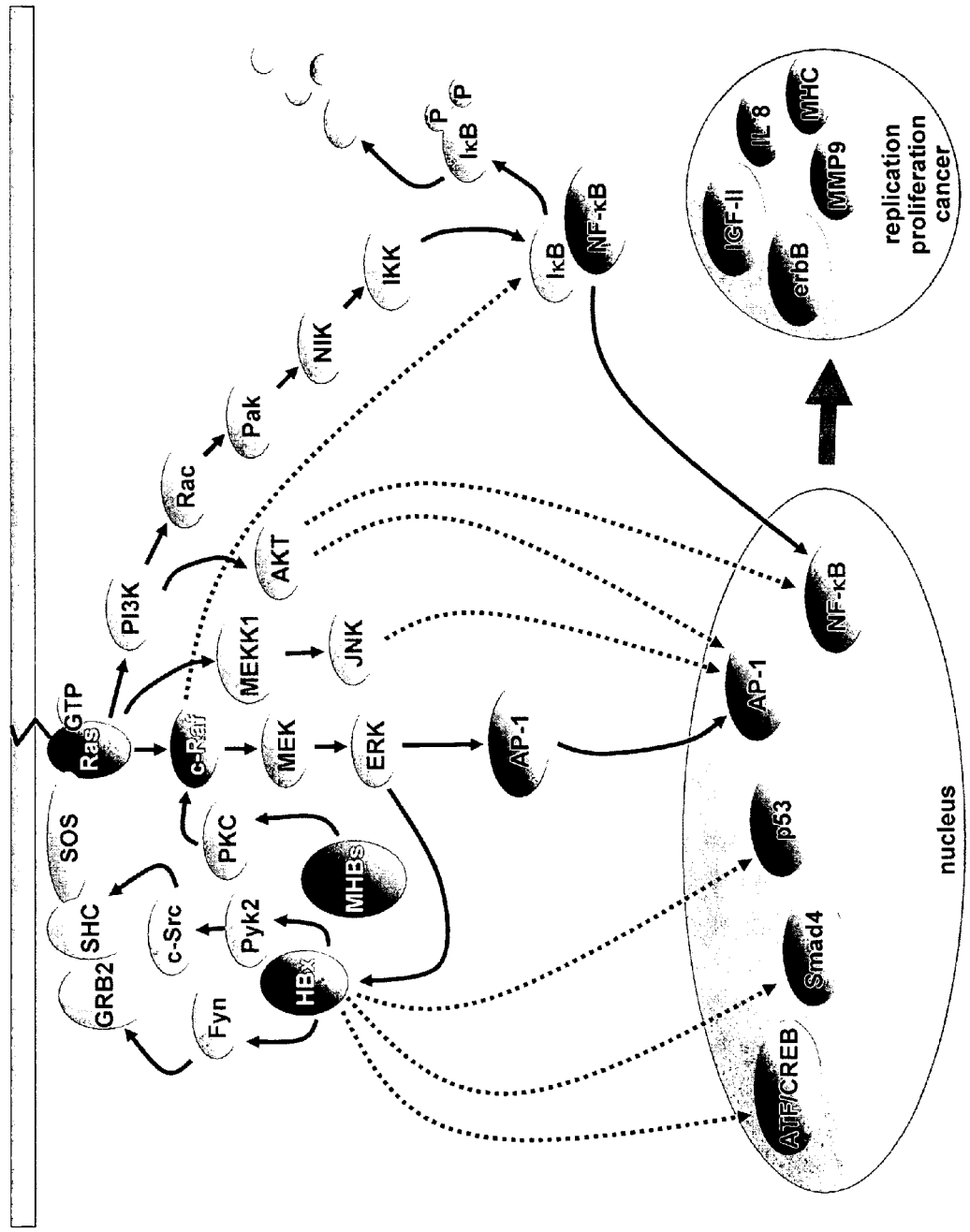
FIG. 3 is a schematic of the signaling cascade that leads to cellular transformation associated with Hepatitis B infection.

Hepatitis B (HBV) virus is small hepatotropic pararetrovirus that causes persistent liver infection and cirrhosis, and is strongly associated with development of primary liver cancer (hepatocellular carcinoma, HCC) (52). HCC is one of the most prevalent forms of human cancer worldwide, with extremely limited treatment options (53). In this regard, many studies have focused on identification of potential viral oncogenes. HBV encodes two transcriptional activators, HBx (54) and the pre-S2/S region of LHB/MHB proteins (55), which activate cellular targets and promote the transformation of infected cells(56). See FIG. 3. The HBx protein of HBV is essential for infection and is also thought to be an essential cofactor in HCC development. The mechanism mediating HBx-dependent activator function includes the Ras-dependent activation of c-Raf-1/MEK/Erk2, PI3K/Akt and MEKK1/JNK cascades, causing induction of several major transcription factors, including AP-1 and NF-κB (57, 58). The HBx protein activates Ras-Raf-MAPK signaling pathway, most likely through activation of the Pyk2 (59), c-Src and Fyn kinases (60). Moreover, the activity and cellular localization of HBx protein is tightly regulated through phosphorylation by ERK1/2 kinase, with such phosphorylation causing the HBx protein to shuttle to the nucleus, where it induces the transcription of genes critical for HBV replication and cell transformation. Thus, the phosphorylation of HBx protein creates a possible feedback regulatory circuit between HBX and MAPK signaling pathway (61), indicating that the MAPK pathway may be a suitable target for developing novel anti-HBV therapeutic agents.

REFERENCES

1. Ablashi, D. V., Chatlynne, L. G., Whitman, J. E., Jr., and Cesarman, E. Spectrum of Kaposi's sarcoma-associated herpesvirus, or human herpesvirus 8, diseases. Clin Microbiol Rev, 15: 439-464, 2002.
2. Gallo, R. C. The enigmas of Kaposi's sarcoma. Science, 282: 1837-1839, 1998.
3. Chang, Y. C., Ethel; Pessin, Melissa S.; Lee, Frank; Culpepper, Janice; Knowles, Daniel M.; Moore, Patrick S. Identification of Herpesvirus-Like DNA Sequences in AIDS-Associated Kaposi's Sarcoma. Science, 266: 1865-1869, 1994.
4. Arvanitakis, L., Geras-Raaka, E., Varma, A., Gershengorn, M. C., and Cesarman, E. Human herpesvirus KSHV encodes a constitutively active G-protein-coupled receptor linked to cell proliferation. Nature, 385: 347-350, 1997.

5. Montaner, S., Sodhi, A., Molinolo, A., Bugge, T. H., Sawai, E. T., He, Y., Li, Y., Ray, P. E., and Gutkind, J. S. Endothelial infection with KSHV genes in vivo reveals that vGPCR initiates Kaposi's sarcomagenesis and can promote the tumorigenic potential of viral latent genes. Cancer Cell, 3: 23-36, 2003.
6. Jenner, R. G. and Boshoff, C. The molecular pathology of Kaposi's sarcoma-associated herpesvirus. Biochim Biophys Acta, 1602: 1-22, 2002.
7. Dadke, D., Fryer, B. H., Golemis, E. A., and Field, J. Activation of p21-activated kinase 1-nuclear factor kappaB signaling by Kaposi's sarcoma-associated herpes virus G protein-coupled receptor during cellular transformation. Cancer Res, 63: 8837-8847, 2003.
8. Cannon, M., Philpott, N. J., and Cesarman, E. The Kaposi's sarcoma-associated herpesvirus G protein-coupled receptor has broad signaling effects in primary effusion lymphoma cells. J Virol, 77: 57-67, 2003.
9. Robinson, M. J. and Cobb, M. H. Mitogen-activated protein kinase pathways. Curr Opin Cell Biol, 9: 180-186, 1997.
10. van Corven, E. J., Hordijk, P. L., Medema, R. H., Bos, J. L., and Moolenaar, W. H. Pertussis toxin-sensitive activation of p21 ras by G protein-coupled receptor agonists in fibroblasts. Proc Natl Acad Sci USA, 90: 1257-1261, 1993.
11. Yart, A., Roche, S., Wetzker, R., Laffargue, M., Tonks, N., Mayeux, P., Chap, H., and Raynal, P. A function for phosphoinositide 3-kinase beta lipid products in coupling beta gamma to Ras activation in response to lysophosphatidic acid. J Biol Chem, 277: 21167-21178, 2002.
12. Kranenburg, O. and Moolenaar, W. H. Ras-MAP kinase signaling by lysophosphatidic acid and other G protein-coupled receptor agonists. Oncogene, 20: 1540-1546, 2001.
13. Lerner, E. C., Qian, Y., Blaskovich, M. A., Fossum, R. D., Vogt, A., Sun, J., Cox, A. D., Der, C. J., Hamilton, A. D., and Sebti, S. M. Ras CAAX peptidomimetic FTI-277 selectively blocks oncogenic Ras signaling by inducing cytoplasmic accumulation of inactive Ras-Raf complexes. J Biol Chem, 270: 26802-26806, 1995.
14. Lyons Jf Fau—Wilhelm, S., Wilhelm S Fau—Hibner, B., Hibner B Fau—Bollag, G., and Bollag, G. Discovery of a novel Raf kinase inhibitor. Endocr Relat Cancer, 8: 219-225, 2001.
15. Allen, L. F., Sebolt-Leopold, J., Meyer, M. B. CI-1040 (PD184352), a targeted signal transduction inhibitor of MEK (MAPKK). Semin Oncol, 30. 105-116, 2003.
16. Bhalla, U. S., Ram, P. T., and Iyengar, R. MAP kinase phosphatase as a locus of flexibility in a mitogen-activated protein kinase signaling network. Science, 297: 1018-1023, 2002.
17. Hofmann, J. Modulation of protein kinase C in antitumor treatment. Rev Physiol Biochem Pharmacol, 142: 1-96, 2001.
18. Wang, X., Wang, Q., Hu, W., and Evers, B. M. Regulation of phorbol ester-mediated TRAF1 induction in human colon cancer cells through a PKC/RAF/ERK/NF-kappaB-dependent pathway. Oncogene, 23: 1885-1895, 2004.
19. Herbst, R. S., Fukuoka, M., and Baselga, J. Gefitinib—a novel targeted approach to treating cancer. Nat Rev Cancer, 4: 956-965, 2004.
20. Attoub S Fau—Rivat, C., Rivat C Fau—Rodrigues, S., Rodrigues S Fau—Van Bocxlaer, S., Van Bocxlaer S Fau—Bedin, M., Bedin M Fau—Bruyneel, E., Bruyneel E Fau—Louvet, C., Louvet C Fau—Kornprobst, M., Komprobst M Fau—Andre, T., Andre T Fau—Mareel, M., Mareel M Fau—Mester, J., Mester J Fau—Gespach, C., and Gespach, C. The c-kit tyrosine kinase inhibitor STI571 for colorectal cancer therapy. Cancer Res, 62: 4879-4883, 2002.
21. Murphy, G. A., Graham, S. M., Morita, S., Reks, S. E., Rogers-Graham, K., Vojtek, A., Kelley, G. G., and Der, C. J. Involvement of phosphatidylinositol 3-kinase, but not RalGDS, in TC21/R-Ras2-mediated transformation. J Biol Chem, 277: 9966-9975, 2002.
22. Safran, H., Iannitti, D., Ramanathan, R., Schwartz, J. D., Steinhoff, M., Nauman, C., Hesketh, P., Rathore, R., Wolff, R., Tantravahi, U., Hughes, T. M., Maia, C., Pasquariello, T., Goldstein, L., King, T., Tsai, J. Y., and Kennedy, T. Herceptin and gemcitabine for metastatic pancreatic cancers that overexpress HER-2/neu. Cancer Invest, 22: 706-712, 2004.
23. Boni, J. P., Leister, C., Bender, G., Fitzpatrick, V., Twine, N., Stover, J., Dorner, A., Immermann, F., and Burczynski, M. E. Population pharmacokinetics of CCI-779: correlations to safety and pharmacogenomic responses in patients with advanced renal cancer. Clin Pharmacol Ther, 77: 76-89, 2005.
24. Pruitt, K., Pruitt, W. M., Bilter, G. K., Westwick, J. K., and Der, C. J. Raf-independent Deregulation of p38 and JNK Mitogen-activated Protein Kinases Are Critical for Ras Transformation. J Biol Chem, 277: 31808-31817, 2002.
25. Sehouli J. Review of gemcitabine-based combinations for platinum-resistant ovarian cancer. Int J Gynecol Cancer, 1: 23-30, 2005.
26. Safran, H., DiPetrillo, T., Nadeem, A., Steinhoff, M., Tantravahi, U., Rathore, R., Wanebo, H., Hughes, M., Maia, C., Tsai, J. Y., Pasquariello, T., Pepperell, J. R., Cioffi, W., Kennedy, T., Reeder, L., Ng, T., Adrian, A., Goldstein, L., Chak, B., and Choy, H. Trastuzumab, paclitaxel, cisplatin, and radiation for adenocarcinoma of the esophagus: a phase I study. Cancer Invest, 22: 670-677, 2004.
27. Polson, A. G., Wang, D., DeRisi, J., and Ganem, D. Modulation of host gene expression by the constitutively active G protein-coupled receptor of Kaposi's sarcoma-associated herpesvirus. Cancer Res, 62: 4525-4530, 2002.
28. Schwarz, M. and Murphy, P. M. Kaposi's sarcoma-associated herpesvirus G protein-coupled receptor constitutively activates NF-kappa B and induces proinflammatory cytokine and chemokine production via a C-terminal signaling determinant. J Immunol, 167: 505-513, 2001.
29. Shepard, L. W., Yang, M., Xie, P., Browning, D. D., Voyno-Yasenetskaya, T., Kozasa, T., and Ye, R. D. Constitutive activation of NF-kappa B and secretion of interleukin-8 induced by the G protein-coupled receptor of Kaposi's sarcoma-associated herpesvirus involve G alpha(13) and RhoA. J Biol Chem, 276: 45979-45987, 2001.
30. Gershengorn, M. C., Geras-Raaka, E., Varma, A., and Clark-Lewis, I. Chemokines activate Kaposi's sarcoma-associated herpesvirus G protein-coupled receptor in mammalian cells in culture. J Clin Invest, 102: 1469-1472, 1998.
31. Montaner, S., Sodhi, A., Pece, S., Mesri, E. A., and Gutkind, J. S. The Kaposi's sarcoma-associated herpesvirus G protein-coupled receptor promotes endothelial cell survival through the activation of Akt/protein kinase B. Cancer Res, 61: 2641-2648, 2001.
32. Bais, C., Van Geelen, A., Eroles, P., Mutlu, A., Chiozzini, C., Dias, S., Silverstein, R. L., Rafii, S., and Mesri, E. A. Kaposi's sarcoma associated herpesvirus G protein-coupled receptor immortalizes human endothelial cells by activation of the VEGF receptor-2/ KDR. Cancer Cell, 3: 131-143, 2003.

33. Montaner, S., Sodhi, A., Servitja, J. M., Ramsdell, A. K., Barac, A., Sawai, E. T., and Gutkind, J. S. The small GTPase Rac1 links the Kaposi sarcoma-associated herpesvirus vGPCR to cytokine secretion and paracrine neoplasia. Blood, 104. 2903-2911, 2004.

34. Dadke, D., Fryer, B. H., Golemis, E. A., and Field, J. Activation of p21-activated kinase 1-nuclear factor kappaB signaling by Kaposi's sarcoma-associated herpes virus G protein-coupled receptor during cellular transformation. Cancer Res, 63: 8837-8847, 2003.

35. Kato-Stankiewicz, J., Hakimi, I., Zhi, G., Zhang, J., Serebriiskii, I., Guo, L., Edamatsu, H., Koide, H., Menon, S., Eckl, R., Sakamuri, S., Lu, Y., Chen, Q. Z., Agarwal, S., Baumbach, W. R., Golemis, E. A., Tamanoi, F., and Khazak, V. Inhibitors of Ras/Raf-1 interaction identified by two-hybrid screening revert Ras-dependent transformation phenotypes in human cancer cells. Proc Natl Acad Sci USA, 99: 14398-14403, 2002.

36. Fahraeus, R., Fu, H. L., Emberg, I., Finke, J., Rowe, M., Klein, G., Falk, K., Nilsson, E., Yadav, M., Busson, P., and et al. Expression of Epstein-Barr virus-encoded proteins in nasopharyngeal carcinoma. Int J Cancer, 42: 329-338, 1988.

37. Klein, G. Viral latency and transformation: the strategy of Epstein-Barr virus. Cell, 58: 5-8, 1989.

38. Pallesen, G., Hamilton-Dutoit, S. J., Rowe, M., and Young, L. S. Expression of Epstein-Barr virus latent gene products in tumour cells of Hodgkin's disease. Lancet, 337: 320-322, 1991.

39. Su, I. J., Hsieh, H. C., Lin, K. H., Uen, W. C., Kao, C. L., Chen, C. J., Cheng, A. L., Kadin, M. E., and Chen, J. Y. Aggressive peripheral T-cell lymphomas containing Epstein-Barr viral DNA: a clinicopathologic and molecular analysis. Blood, 77: 799-808, 1991.

40. Karp, J. E., and Broders, S. Acquired immunodeficiency syndrom and non-Hodgkin's lymphomas. Cancer Res., 51: 4743-4756, 1991.

41. Ho, M., Miller, G., Atchison, R. W., Breinig, M. K., Dummer, J. S., Andiman, W., Starzl, T. E., Eastman, R., Griffith, B. P., Hardesty, R. L., Bahnson, H. T., Hakala, T. R., and Rosenthal, J. T. Epstein-Barr virus infections and DNA hybridization studies in posttransplant lymphoma and lymphoproliferative lesions: The role of primary infection. J. Infect. Dis., 152. 876-886, 1985.

42. Wang, D., Liebowitz, D., and Kieff, E. An EBV membrane protein expressed in immortalized lymphocytes transforms established rodent cells. Cell, 43: 831-840, 1985.

43. Kulwichit W, Edwards R. H., and M., D. E. Expression of the Epstein-Barr virus latent membrane protein 1 induces B cell lymphoma in transgenic mice. Proc Natl Acad Sci USA, 95: 11963-11968, 1998.

44. Lo, A. K., Liu, Y., Wang, X. H., Huang, D. P., Yuen, P. W., Wong, Y. C., and Tsao, G. S. Alterations of biologic properties and gene expression in nasopharyngeal epithelial cells by the Epstein-Barr virus-encoded latent membrane protein 1. Lab Invest, 83: 697-709, 2003.

45. Roberts, M. L. and Cooper, N. R. Activation of a ras-MAPK-dependent pathway by Epstein-Barr virus latent membrane protein 1 is essential for cellular transformation. Virology, 240: 93-99, 1998.

46. Kaye, K. M., Devergne, O., Harada, J. N., Izumi, K. M., Yalamanchili, R., Kieff, E., and Mosialos, G. Tumor necrosis factor receptor associated factor 2 is a mediator of NF-kappa B activation by latent infection membrane protein 1, the Epstain-Barr virus transforming protein. Proc Natl Acad Sci USA, 93: 11085-11090, 1996.

47. Izumi, K. M. and Kieff, E. D. The Epstein-Barr virus oncogene product latent membrane protein 1 engages the tumor necrosis factor receptor-associated death domain protein to mediate B lymphocyte growth transformation and activate NF-kappaB. Proc Natl Acad Sci USA, 94: 12592-12597, 1997.

48. Mosialos, G., Birkenbach, M., Yalamanchili, R., VanArsdale, T., Ware, C., and Kieff, E. The Epstein-Barr virus transforming protein LMP 1 engages signaling proteins for the tumor necrosis factor receptor family. Cell, 80. 389-399, 1995.

49. Sylla, B. S., Hung, S. C., Davidson, D. M., Hatzivassiliou, E., Malinin, N. L., Wallach, D., Gilmore, T. D., Kieff, E., and Mosialos, G. Epstein-Barr virus-transforming protein latent infection membrane protein 1 activates transcription factor NF-kappaB through a pathway that includes the NF-kappaB-inducing kinase and the IkappaB kinases IKKalpha and IKKbeta. Proc Natl Acad Sci USA, 95: 10106-10111, 1998.

50. Yeung, K. C., Rose, D. W., Dhillon, A. S., Yaros, D., Gustafsson, M., Chatterjee, D., McFerran, B., Wyche, J., Kolch, W., and Sedivy, J. M. Raf kinase inhibitor protein interacts with NF-kappaB-inducing kinase and TAKI and inhibits NF-kappaB activation. Mol Cell Biol, 21: 7207-7217, 2001.

51. Jones, W. K., Brown, M., Ren, X., He, S., and McGuinness, M. NF-kappaB as an integrator of diverse signaling pathways: the heart of myocardial signaling? Cardiovasc Toxicol, 3: 229-254, 2003.

52. Ganem, D. and Varmus, H. E. The molecular biology of the hepatitis B viruses. Annu Rev Biochem, 56: 651-693, 1987.

53. Beasley, R. P., Hwang, L. Y., Lin, C. C., and Chien, C. S. Hepatocellular carcinoma and hepatitis B virus. A prospective study of 22 707 men in Taiwan. Lancet, 2. 1129-1133, 1981.

54. Twu, J. S. and Schloemer, R., H. Transcriptional transactivating function of hepatitis B virus. J. Virol., 61: 3448-3453, 1987.

55. Kekule, A. S., Lauer, U., Meyer M., Caselmann, W. H., Hofschneider, P. H., and R., K. The preS2/S region of integrated hepatitis B virus DNA encodes a trancriptional transactivator. Nature, 343: 457-461, 1990.

56. Stockl, L., Berting, A., Malkowski, B., Foerste, R., Hofschneider, P. H., and Hildt, E. Integrity of c-Raf-1I/MEK signal transduction cascade is essential for hepatitis B virus gene expression. Oncogene, 22: 2604-2610, 2003.

57. Benn, J. and Schneider, R. J. Hepatitis B virus HBx protein activates Ras-GTP complex formation and establishes a Ras, Raf, MAP kinase signaling cascade. Proc Natl Acad Sci USA, 91: 10350-10354, 1994.

58. Chung, T. W., Lee, Y. C., and Kim, C. H. Hepatitis B viral HBx induces matrix metalloproteinase-9 gene expression through activation of ERK and PI-3K/AKT pathways: involvement of invasive potential. Faseb J, 18: 1123-1125, 2004.

59. Bouchard, M. J., Wang, L. H., and Schneider, R. J. Calcium signaling by HBx protein in hepatitis B virus DNA replication. Science, 294: 2376-2378, 2001.

60. Klein, N. P. and Schneider, R. J. Activation of Src family kinases by hepatitis B virus HBx protein and coupled signaling to Ras. Mol Cell Biol, 17: 6427-6436, 1997.

61. Noh, E. J., Jung, H. J., Jeong, G., Choi, K. S., Park, H. J., Lee, C. H., and Lee, J. S. Subcellular localization and transcriptional repressor activity of HBx on p21 (WAF1/

Cip1) promoter is regulated by ERK-mediated phosphorylation. Biochem Biophys Res Commun, 319: 738-745, 2004.

While certain preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A compound of the formula

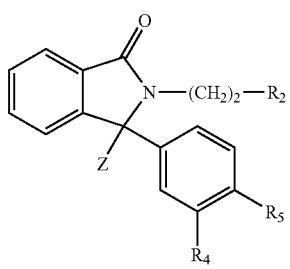

(I)

, including enantiomeric and diastereomeric isomers thereof and mixtures of said isomers,
wherein
Z is —H, —OH, alkoxy;
$R_2$ is an optionally substituted heteroaryl or heterocycloalkyl group the optional substituents being at least one selected from the group consisting of halogen atom, $NH_2$, SH, $NO_2$, OH, unsubstituted alkyl, heteroalkyl, aryl, aralkyl, aralkyloxy, heteroaryl, cycloalkyl or heterocycloalkyl group;
$R_4$ is H, alkoxy or aralkoxy; and
$R_5$ is F, Cl, alkyl, heteroalkyl, aryl, aralkyl, heteroaryl or heteroarylalkyl, and the pharmacologically acceptable salts of said compounds.

2. A method for the treatment of viral infection in a patient in need thereof, said virus being selected from the group consisting of HHV-8, HHV-4 and hepatitis B virus, said method comprising administering to said patient a therapeutically effective amount of a compound of claim 1.

3. The method of claim 2, further comprising the administration of a mitogen activated protein kinase (MAPK) pathway inhibitor and optionally an antiproliferative agent.

4. The method of claim 3, wherein said MAPK pathway inhibitor is selected from the group of Bay 43-9006, CI-1040, AA-COCF3, Bryostatin, gefitinib, LY 294002, SP 600125.

5. The method of claim 3, further comprising administration of said antiproliferative agent, said anti-proliferative agent being selected from the group of FTI 227, Bay 43-9006, CI-1040, AA-COCF3, Bryostatin, gefitinib, imatinib methanesulfonate, LY 294002, rhu Mab HER2, rapamycin, (rapamycin analog CCI-779), SP 600125, Gemcitabine and Paclitaxel.

6. A pharmaceutical composition comprising a therapeutically effective amount of a compound according to claim 1 and a pharmaceutically acceptable carrier, said composition optionally comprising an antiproliferative agent or mitogen activated protein kinase (MAPK) pathway inhibitor selected from the group of FTI 227, Bay 43-9006, CI-1040, AA-COCF3, Bryostatin, gefitinib, imatinib methanesulfonate, LY 294002, rhu Mab HER2, rapamycin, (rapamycin analog CCI-779), SP 600125, Gemcitabine and Paclitaxel.

7. A compound of claim 1, selected from the group consisting of 3-(4-Benzyloxy-3-methoxy-phenyl)-3-methoxy-2-(2-pyridin-2-yl-ethyl)-2,3-dihydro-isoindol-1-one; and
3-(4-Benzyloxy-3-methoxy-phenyl)-2-(2-pyridin-2-yl-ethyl)-2,3-dihydro-isoindol-1-one.

8. A compound of the formula:

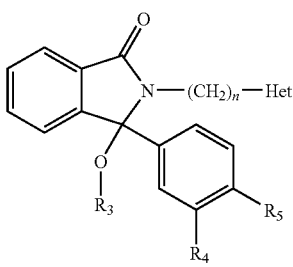

, including enantiomeric and diastereomeric isomers thereof and mixtures of said isomers,
wherein Het is a pyridyl group; n is 0,1 or 2; $R_3$ is alkyl; $R_4$ is H, alkoxy or aralkoxy and $R_5$ is F, Cl, alkyl, heteroalkyl, aryl, aralkyl, heteroaryl or heteroarylalkyl group, and the pharmacologically acceptable salts of said compound.

9. The compound of claim 8, wherein each of $R_4$ and $R_5$ is methoxy or benzyloxy.

10. A compound of the formula:

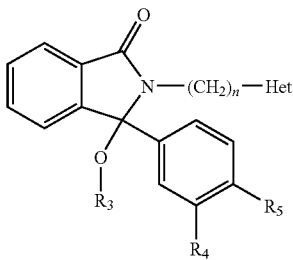

, including enantiomeric and diastereomeric isomers thereof and mixtures of said isomers,
wherein Het is a piperidyl group; n is 0, 1 or 2; $R_3$ is alkyl; $R_4$ is H, alkoxy or aralkoxy and $R_5$ is F, Cl, alkyl, heteroalkyl, aryl, aralkyl, heteroaryl or heteroarylalkyl, and the pharmacologically acceptable salts of said compounds.

11. The compound of claim 10, wherein each of $R_4$ and $R_5$ is methoxy or benzyloxy.

* * * * *